United States Patent [19]

Allen

[11] 4,393,054

[45] Jul. 12, 1983

[54] METHOD OF TREATING CARDIAC ARRHYTHMIA

[75] Inventor: Harry R. Allen, Texas Township, Kalamazoo County, Mich.

[73] Assignee: The Upjohn Company, Kalamazoo, Mich.

[21] Appl. No.: 379,528

[22] Filed: May 19, 1982

[51] Int. Cl.$^3$ ...................... A61K 31/71; C07H 15/16
[52] U.S. Cl. .................................. 424/180; 536/16.2; 536/16.5; 536/27
[58] Field of Search ............................. 536/16.2, 16.5; 424/180

[56] References Cited

U.S. PATENT DOCUMENTS 3,671,647  6/1972  Argoudelis et al. ................ 424/180
4,278,789  7/1981  Birkenmeyer ...................... 536/16.4

OTHER PUBLICATIONS

Opie et al., "Chem. Abst.", vol. 93, 1980, p. 130110s.

*Primary Examiner*—Johnnie R. Brown
*Attorney, Agent, or Firm*—Roman Saliwanchik

[57] ABSTRACT

The 3-(5'-adenylate) of lincomycin- and clindamycin-type compounds in which the propyl hygric acid moiety has been replaced by different cyclic amino acids can be used to treat cardiac arrhythmia in humans and animals.

3 Claims, No Drawings

METHOD OF TREATING CARDIAC ARRHYTHMIA

BACKGROUND OF THE INVENTION

The characteristics and preparation of the antibiotic lincomycin are disclosed in U.S. Pat. No. 3,086,912. Clindamycin is disclosed in U.S. Pat. No. 3,496,163. These antibiotics have been extensively used as medicines in humans and animals. A number of patents world-wide have issued concerning these antibiotics and a variety of derivatives thereof.

The structural formulas for lincomycin (1) and clindamycin (2) are shown in Chart 1.

The lincomycin- and clindamycin-type compounds which can be converted to the 3-(5'-adenylate) are shown in Chart 2. In place of the hydroxyl at the three position of the lincosaminide moiety, there is substituted the adenylate residue.

The 3-(5'-adenylate) of the subject invention can be prepared by microbiological transformation procedures. A 3-(5'-adenylate) is shown in Chart 3. This compound, designated U-63,440, is used to exemplify the other compounds which are within the scope of the subject invention, as shown in Chart 2.

BRIEF SUMMARY OF THE INVENTION

Upon administering an effective amount of a compound of the formula as shown in Chart 2 to a human or animal in need of treatment for cardiac arrhythmia, the desired effect is obtained. An effective amount is recognized as an inhibiting quantity to treat cardiac arrhythmia. This effect of the compounds of the subject invention is unexpected and surprising since the compounds were previously known only for their antibiotic properties. There is nothing in the prior art which suggests this utility for the invention compounds.

DETAILED DISCLOSURE OF THE INVENTION

Preparation of the Invention Compounds

The parent compounds disclosed in Chart 2, i.e., those without the adenylate moiety, can be prepared by the procedures disclosed in U.S. Pat. No. 4,278,789.

The required aminosugar starting materials are known in the art. Some of these starting materials can be advantageously prepared by the well known hydrazinolysis of acylamino sugars. The starting materials wherein $R_{12}$ is methyl are disclosed in U.S. Pat. Nos. 4,278,789, 3,702,322, 3,915,954, and 3,502,648. The starting materials wherein $R_{12}$ is ethyl are disclosed in U.S. Pat. Nos. 3,361,628, 3,380,992, 3,502,648, 3,702,322, and 3,915,954. The starting materials wherein $R_{12}$ is 2-hydroxyethyl are disclosed in U.S. Pat. Nos. 3,380,992, 3,817,979, 3,208,996, and 3,915,954. The compounds of this invention wherein $R_{12}$ is

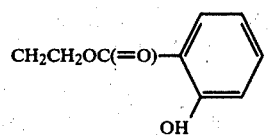

are best prepared by esterifying the appropriate hydroxyl group of the corresponding compound wherein $R_{12}$ is $CH_2CH_2OH$. This esterification can be performed on either the amino sugar or the acylamino sugar and may require protection methods well known in the art.

The 3-(5'-adenylates) of the compounds of Chart 2 can be prepared by following the procedures disclosed in U.S. Pat. No. 3,671,647. Salts of these compounds also can be prepared following the procedures in U.S. Pat. No. 3,671,647.

The dosage range for using the compounds of the subject invention to treat cardiac arrhythmia in humans and animals is from about 1 to about 100 mg/kg. Dosage amount and frequency can be varied as required by the condition of the patient to achieve the desired effect. Administration would be as usual for anti-arrhythmic use, e.g. by oral, parenteral including intravenous and intramuscular routes. Administration could be by continuous infusion or by periodic dosing. For example, according to Goodman and Gilman's *The Pharmacological Basis of Therapeutics* (Sixth Edition, MacMillan Publishing Co., Inc., New York 1980, page 781), 1 to 2 mg/kg of lidocaine is administered for antiarrhythmic effect by intravenous injection, followed in 20 to 40 minutes by a second injection of half the size of the first. Constant intravenous infusion of 1 to 5 mg/minute of lidocaine produces therapeutic concentrations in plasma of 1 to 5 µg/ml. Lidocaine can also be given intramuscularly at doses of 4 to 5 mg/kg to produce an effective plasma concentration within 15 minutes, the effect lasting for about 90 minutes. Depending on the condition of the patient, the compounds of this invention being used, and other factors of concern to an attending physician, the appropriate dosage amount and schedule can be determined to achieve the desired antiarrhythmic effect.

EXAMPLE 1

Capsules

One thousand two-piece hard gelatin capsules for oral use, each containing 50 mg of U-63,440, are prepared from the following types and amounts of materials:

| | |
|---|---|
| U-63,440 | 50 gm |
| Corn starch | 100 gm |
| Talc | 75 gm |
| Magnesium stearate | 25 gm |

The materials are thoroughly mixed and then encapsulated in the usual manner.

The foregoing capsules are useful for the systemic treatment of cardiac arrhythmia in adult humans by oral administration of one capsule every 3 to 6 hours.

Using the procedure above, capsules are similarly prepared containing U-63,440 in 10, 25, and 100 mg amounts by substituting 10, 25, and 100 gm of U-63,440 for the 50 gm used above.

EXAMPLE 2

Tablets

One thousand tablets for oral use, each containing 50 mg of U-63,440, are prepared from the following types and amounts of materials:

| | |
|---|---|
| U-63,440 | 50 gm |
| Lactose | 125 gm |
| Corn starch | 65 gm |
| Magnesium stearate | 25 gm |

-continued

| Light liquid petrolatum | 3 gm |

The ingredients are thoroughly mixed and slugged. The slugs are broken down by forcing through a number 16 screen. The resulting granules are then compressed into tablets, each tablet containing 50 mg of U-63,440.

The foregoing tablets are useful for treatment of adult humans by oral administration of one tablet three times a day.

Using the above procedure, except for reducing the amount of U-63,440 to 25 gm, tablets containing 25 mg of U-63,440 are prepared.

EXAMPLE 3

Oral Syrup

One thousand cc of an aqueous suspension for oral use, containing in each 5 cc dose 100 mg of U-63,440 is prepared from the following types and amounts of ingredients:

| U-63,440 | 20 gm |
| Citric acid | 2 gm |
| Benzoic acid | 1 gm |
| Sucrose | 700 gm |
| Tragacanth | 5 gm |
| Lemon oil | 2 cc |
| Deionized water, q.s. | 1000 cc |

The citric acid, benzoic acid, sucrose, tragacanth, and lemon oil are dispersed in sufficient water to make 850 cc of solution. The U-63,440 is stirred into the syrup until uniformly distributed. Sufficient water is added to make 1000 cc.

The composition so prepared is useful to treat cardiac arrhythmia in adult humans at a dose of 1 tablespoonful (10 cc) 4 times a day.

EXAMPLE 4

Parenteral Solution

A sterile aqueous solution for intramuscular use, containing 100 mg of U-63,440 in 1 cc is prepared from the following types and amounts of materials:

| U-63,440 | 100 gm |
| Methylparaben | 2.5 gm |
| Propylparaben | 0.17 gm |
| Water for injection, q.s. | 1,000 cc |

The ingredients are dissolved in the water and the solution sterilized by filtration. The sterile solution is filled into vials and the vials sealed.

EXAMPLE 5

Following the procedure of each of the preceding Examples 1–4, inclusive, each active compound of the subject invention is substituted in an equivalent amount for the U-63,440 shown in the example to provide therapeutic properties.

Similarly, each of the above free base compounds can be used in the form of a pharmaceutically (or pharmacologically) acceptable salt, e.g., hydrochloride, sulfate, phosphoric, sodium, potassium, calcium, and lithium.

CHART 1

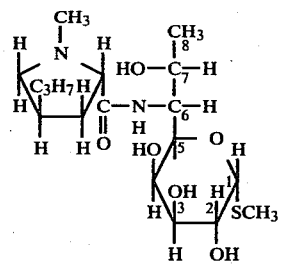

(1)

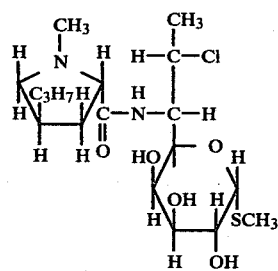

(2)

CHART 2

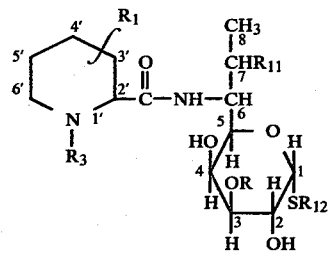

wherein R is

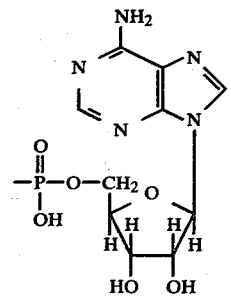

$R_1$ is H, $C_1$—$C_8$—alkyl;
$R_{11}$ is OH, OCH$_3$, halogen (Cl, Br, I),
—SCH$_2$CH$_2$OH, —SCH$_2$CH$_2$CH$_2$OH, SCH$_3$;
$R_{12}$ is CH$_3$, —CH$_2$CH$_3$, —CH$_2$CH$_2$OH,

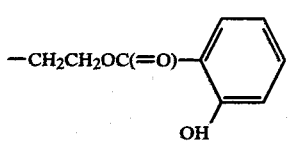

CHART 3

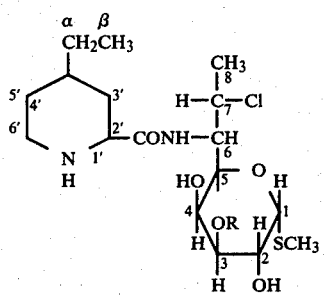

where R is

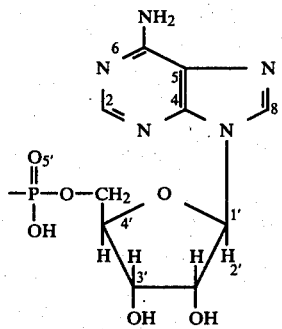

I claim:

1. The method for the treatment of cardiac arrhythmia in a patient which comprises administering a pharmaceutical carrier and a cardiac arrhythmia inhibiting quantity of a compound of the formula

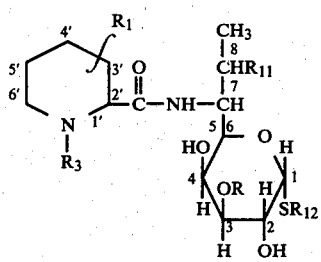

wherein R is

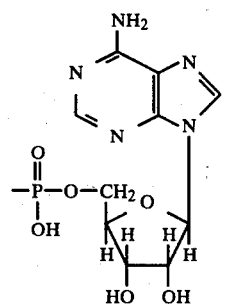

$R_1$ is H, $C_1$-$C_8$-alkyl; $R_{11}$ is OH, OCH$_3$, halogen (Cl, Br, I), —SCH$_2$CH$_2$OH, —SCH$_2$CH$_2$CH$_2$OH, SCH$_3$; $R_{12}$ is CH$_3$, CH$_2$CH$_3$, —CH$_2$CH$_2$OH,

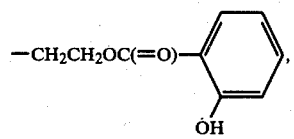

or the pharmaceutically acceptable acid addition salts thereof.

2. The method, according to claim 1, wherein said inhibiting quantity is from about 1 to about 100 mg/kg.

3. The method, according to claim 1, wherein said administered compound has the formula

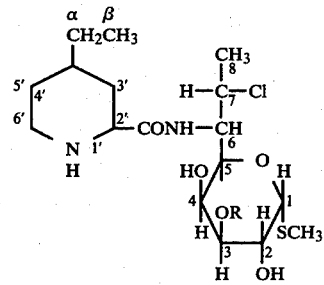

wherein R is

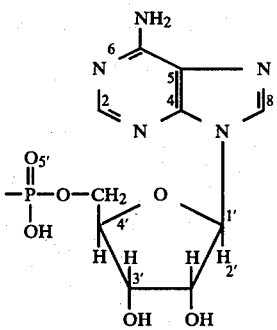

* * * * *